United States Patent [19]
Abrams et al.

[11] Patent Number: 4,727,068
[45] Date of Patent: Feb. 23, 1988

[54] RADIOSENSITIZATION BY COBALT AND FE(III) COMPLEXES

[75] Inventors: Michael Abrams, Glenmoore, Pa.; Beverly Teicher, Needham, Mass.

[73] Assignee: Johnson Matthey, Inc., Malvern, Pa.

[21] Appl. No.: 790,528

[22] Filed: Oct. 23, 1985

[51] Int. Cl.4 ............................................. A61N 5/10
[52] U.S. Cl. ................................... 514/184; 514/185; 514/188
[58] Field of Search ....................... 514/184, 185, 188

[56] References Cited

U.S. PATENT DOCUMENTS 3,017,325  1/1962  Vogel ................................. 514/185
4,569,932  2/1986  Bergquist et al. ................... 514/185

Primary Examiner—Earl Nielsen
Attorney, Agent, or Firm—Cushman, Darby & Cushman

[57] ABSTRACT

Hypoxic cells are rendered more sensitive to destruction by X-rays or other high energy radiation by treatment with cobalt or iron coordination compounds.

4 Claims, No Drawings

RADIOSENSITIZATION BY COBALT AND FE(III) COMPLEXES

The present invention relates to radiosensitization and, more particularly, to rendering hypoxic cells more sensitive to being killed by X-rays or other forms of irradiation.

BACKGROUND TO THE INVENTION

One established form of cancer treatment is irradiation by high-energy electromagnetic waves, typically X-rays. Solid tumors contain significant numbers of cells which are distal from the vasculature leading to oxygen deficiency or hypoxia. Hypoxia protects cells from radiotherapy. There is, therefore, a need for compounds which render the hypoxic cells more sensitive to killing by X-rays or the like. These compounds will be referred to herein as "radiosensitizers".

A variety of transition metal complexes have been shown to possess radiosensitizer activity. These include complexes of Ag, Cu, Zn, Hg, Pt, Co, Fe and Rh—1-13. The present invention is based on the finding that certain coordination compounds of cobalt and iron, namely Co(III) and Fe(III) coordination compounds, are potentially useful as radiosensitizers.

DESCRIPTION OF THE INVENTION

More particularly, the Co(III) or Fe(III) compounds contemplated for use herein may be selected from (1) compounds having the formula:

$$[CoN_nX_{6-n}]^y \qquad (1)$$

where
n has a value of 3 or 4;
N is an uncharged nitrogen donor atom that is contained within a ligand;
X represents an anionic ligand; and
y represents the charge on the complex;
(2) compounds having the formula:

$$[CoA_2X^1D]^{y_1} \qquad (2)$$

where
A represents a bidentate or tetradentate negative ligand containing N or O donor atoms;
$X^1$ and D represent the same or different monodentate ligands; and
$y^1$ represents a positive or negative charge on the complex;
(3) compounds having the formula:

$$[CoZ_3] \qquad (3)$$

where Z represents a chelating mononegative negative ligand; and
(4) compounds of the formula:

$$[Fe\ TT^1]^+ \qquad (4)$$

where T and $T^1$, which may be the same or different, represent mono-negative tridentate ligands.

Typically, when L is an uncharged nitrogen donor ligand, it is ammonia, mono-or-di-alkylamine, a heterocyclic ring such as substituted or unsubstituted pyridine, imidazole or aziridine.

L may also be a chelating diamine such as ethylenediamine, 1,10-phenanthroline and 2,2'-bipyridine, triamines such as diethylenetriamine and 1,4,7-triazacylononane, and tetramines such as triethylenetetramine.

Representative values for X include nitrate, nitrite, sulphate, halide, thiocyanate, azide, cyanide, acetate, malonate or oxalate.

As noted, y represents the charge on the complex and usually is +1 or 0. Where y is +1, the compound includes a complex cation and the counter ion may be halide, sulphate, nitrate or other like anion.

With respect to the compounds of formula (2), representative examples of A include dimethylglyoxime and any B-diketonate such as acetylacetone (acac). The A substituent can also be a tetradentate dinegative ligand of the Schiff base variety:

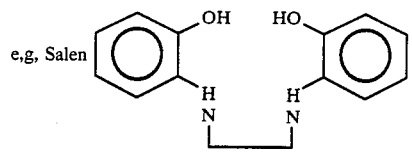

e,g, Salen

X' and D, which may be the same or different monodentate ligands, can be charged or uncharged. Typical examples of these substituents include pyridine, nitrite, halide, aziridine, substituted imidazole, alkyl amine and the like.

Where $y^1$ is negative, the compound includes a complex anion and the counter ion may be selected from ammonium, sodium, potassium or the like. Where $y^1$ is positive, the compound includes a complex cation and the counter ion may be selected from halide, sulphate, or other like anions.

As for compounds (3), Z may be, inter alia, an amino acid or a B-diketonate.

T and $T^1$, in the case of the compounds (4), represent mono-negative, tridentate ligands such as cyclopentadienyl, substituted cyclopentadienyl, hydro-tris (pyrazoyl) borate, alkyl-tris (pyrazolyl) borate and substituted analogs of the indicated borates.

Specific examples of compounds which may be used as sensitizers according to the invention include the following:
$Co(NH_3)_3X_3$ where X is $NO_2^-$ or $CN^-$
[Co(1,10-phenanthroline)$_2X_2$]$NO_3$ where X is $NO_2^-$, $CN^-$ or halide
[Co(aziridine)$_4(NO_2)_2$]Br
[Co(ethylenediamine)$_2X_2$]X where X is $NO_2^-$ or halide
[Co(DH)$_2$(pyridine)Cl] where DH stands for the anion of dimethylglyoxime
[Co(DH)$_2$(aziridine)$_2$]Cl
Co(glycine)$_3$
Co(2,4-pentandionato)$_3$
[Co(pentanedionato)$_2(NO_2)$(pyridine)]
Co(dien)(NO$_2$)$_3$ where dien is diethylenetriamine
[Fe(C$_2$H$_5$)$_2$]X where X is an anion such as a halide, $NO_3^-$, $CCl_3CO_2$
[Fe(HB(PYZ)$_3$)]X where HB(PYZ)$_3$ is hydrotris pyrazolylborate The above compounds are known and their preparation is shown in the chemical literature.

The invention contemplates not only the use of the above noted categories of compounds for use as radiosensitizers but pharmaceutical compositions for such use including the indicated compounds as the effective radiosensitizing agent, together with a pharmaceutically-acceptable solid or liquid carrier, diluent or excipient therefor. These compositions may take any of the conventional forms for effective administration, e.g. pills, tablets, sterile injectable solutions and the like, containing an effective amount of one or more of the indicated compounds of formulas (1) to (4). Usually the amount of such compound or compounds contained in such compositions will fall in the range of 0.1 to 5% by weight or even more (e.g. 20%), based on the total weight of the composition.

The indicated composition may be used in conventional manner for radiosensitizing purposes in combination with irradiation or the like in the treatment of cancer. Preferably the compound is administered before irradiation in the usual amounts to effect radiosensitization although the administration may also occur concurrently with the radiation.

Radiosensitizers for use according to the invention may be evaluated in toxicity and radiosensitization screens. The toxicity screen is used to evaluate the cytotoxicity of the compound itself. The method of testing is as follows:

Cells—The EMT6 mammary tumor cell line is well established and has been widely used for the study of hypoxic cells. See Laboratory Animal Science 27:831-851 (1977). These experiments were performed using asynchronous EMT6-BT monolayers in exponential growth in Waymouth's medium supplemented with antibiotics and 15% newborn calf serum. This cell line has a plating efficiency of 65-80% and a doubling time of 16-19 hrs. in vitro. See J. Natl. Cancer Inst. 49:735-474 (1972). The cells begin to show a measurable reduction in survival from hypoxic stress alone after approximately 8-9 hr in a hypoxic atmosphere. See Radiat. Res., 53:281-294 (1973).

Radiosensitization Studies—To produce hypoxia, plastic flasks, containing exponentially-growing monolayers in complete medium plus serum, were fitted with sterile rubber septums and exposed to a continuously-flowing 95% nitrogen/5% $CO_2$ humidified atmosphere for 4 hr at 37° C. Parallel flasks were maintained in 95% air/5% $CO_2$. At the end of 4 hr, the drug or vehicle was added to the flasks by injection through the rubber septum without disturbing the hypoxia. A drug dose of 100 $\mu$M was selected to produce minimal toxicity from the drug alone under the conditions of the experiments. Oxic or hypoxic conditions were maintained throughout the 1 hour drug exposure at 37° C. and the irradiation was obtained using a cesium 137 irradiation unit at a dose rate of approximately 1.05 Gy/min. at 25° C. Drug treated cells were irradiated so that the irradiation would be completed 1 hour after addition of the drug. X-ray doses of 500, 1000, 1500 and 2000 rads were used. After treatment, the monolayers were washed with sterile phosphate buffered saline. The cells were suspended by trypsinization, counted with a counter, then diluted with complete medium. Three different volumes of the cell suspension were plated in duplicate on dishes containing complete medium. Dishes were incubated for 8-10 days under standard cell culture conditions to allow clonogenic cells to grow into macroscopic colonies. The colonies were visualized by staining with crystal violet in methanol containing 3.7% formaldehyde and were counted manually. Each experiment was repeated three times.

Baseline curves for irradiation of the cells under oxic and hypoxic conditions in the absence of the compounds were also determined to allow a quantitative estimation of the efficiency of the compound in sensitizing the cells to radiation-induced killing. This quantification may be expressed in the form of an enhancement ratio calculated from the slope of the survival curve in the presence of the compound divided by the slope of the survival curve in the absence of the compound.

Cytotoxicity—To measure cytotoxicity, varying concentrations of drug (50, 100 and 500 $\mu$M) was added to exponentially growing EMT6 cells maintained under hypoxic conditions or oxygenated conditions. After 1 hr, cells were washed, suspended and plated as described above. Correction for cell killing due to hypoxia was made in the hypoxic cell survival curve. As in the single time exposure experiments, each cytotoxicity time course experiment was repeated three times.

The invention is illustrated by the following examples:

EXAMPLE 1

Preparation of trans-[Co(NH$_3$)$_4$(NO$_2$)$_2$]X where X is NO$_3^-$ or CH$_3$CO$_2^-$ from G. S. Schessinger, "Inorganic Laboratory Preparations" Chemical Publishing Company, Inc., N.Y., 1962, P. 246.

A solution of CoCl$_2$·6H$_2$O (18.0 g) in water (50 mL) was prepared and added to a solution of NH$_4$Cl (20.0 g), NaNO$_2$ (27.0 g), and concentrated aqueous ammonia (20 mL) in water (150 mL). Air was bubbled through this solution for 4 hrs. and the reaction mixture was allowed to stand in the dark overnight. The yellow product was collected and washed with cold water (3×10 mL). This material was added to a hot (60° C.) solution of acetic acid (1 mL) in water (400 mL). After being stirred for 5 min., the solution was filtered and NH$_4$NO$_3$ was added to the filtrate. The resulting yellow crystalline product was collected, washed with cold water (15 mL), ethanol (20 mL) and either (20 mL) and dried in vacuo. Yield=11.4 g of trans-[Co(NH$_3$)$_4$(NO$_2$)$_2$]NO$_3$.

The acetate salt can be prepared by using NH$_4$CH$_3$CO$_2$ instead of NH$_4$NO$_3$ in the last step.

Analysis of acetate salt:

|         | C    | H    | N     |
|---------|------|------|-------|
| % Calc. | 8.67 | 5.44 | 30.22 |
| % Found | 8.42 | 5.47 | 29.95 |

EXAMPLE 2

This example describes the preparation of [(C$_2$H$_5$)Fe]CCl$_3$CO$_2^-$·2CCl$_3$CO$_2$H according to D.N. Hendrickson et al., J. Chem. Phys. 58, 1973, 4666.

Ferrocene (3.0 g) and trichloroacetic acid (7.9 g) were dissolved in benzene (50 mL). Air was bubbled through the solution for 1 hr. and then the solution was stoppered and placed in a refrigerator (5° C.) overnight. The product was collected, washed with benzene (10 mL) and dried in vacuo.

Analysis :

|         | C     | H    | N     |
|---------|-------|------|-------|
| % Calc. | 28.46 | 1.79 | 47.25 |
| % Found | 28.19 | 1.81 | 47.52 |

EXAMPLE 3

This example illustrates the preparation of cis-[Co(1,10-phenanthroline)$_2$(NO$_2$)$_2$]NO$_3$ H$_2$O according to A. V. Ablov, *Russ. J. Inorg. Chem.*, 6, 1961, 157.

To a solution of Co(NO$_3$)$_2$6H$_2$O (2.9 g) and NaNO$_2$ (3.0 g) in water (40 mL) was added a solution of phenanthroline hydrate (3.9 g) in ethanol (20 mL). A small quantity (0.5 mL) of acetic acid was added and the reaction mixture was stirred for 10 min. The product was collected and recystallized from hot water containing an excess of NaNO$_3$. Yield Analysis:

|        | C     | H    | N     |
|--------|-------|------|-------|
| % Calc.| 47.30 | 3.31 | 16.09 |
| % Found| 47.04 | 3.31 | 16.01 |

EXAMPLE 4

The products of Examples 1 to 3 may be checked for radiosensitization and cytotoxicity using the procedure outlined above under the heading "Radiosensitization Studies", and "Cytotoxicity". Administration of the compounds followed by irradiation as described shows a very marked reduction in the survival fraction of hypoxic cells as well as oxic cells. The compounds may thus be effectively used as radiosensitizers in combination with irradiation.

It will be recognized that various modifications may be made in the invention as described above. Accordingly, the scope of the invention is defined in the following claims.

We claim:

1. A method for rendering hypoxic cells more sensitive to irradiation which comprises subjecting the cells to treatment with a Co(III) or Fe(III) coordination compound selected from the group consisting of:

(1) compounds having the formula:

$$[CoN_nX_{6-n}]^y \qquad (1)$$

where
    n has a value of 3 or 4;
    N is an uncharged nitrogen donor atom that is contained in a ligand;
    X represents an anionic ligand; and
    y represents the charge on the complex;

(2) compounds having the formula:

$$[CoA_2X^ID]^{y_1} \qquad (2)$$

where
    A represents a bidentate or tetradentate negative ligand containing N or O donor atoms;
    $X^1$ and D represent the same or different monodentate ligands; and
    $y^1$ represents a positive or negative charge on the complex;

(3) compounds having the formula:

$$[CoZ_3] \qquad (3)$$

where Z represents a chelating mononegative negative ligand; and (4) compounds of the formula:

$$[Fe\ TT^1]^+ \qquad (4)$$

where T and $T^1$, which may be the same or different, represent mono-negative tridentate ligands.

2. The method of claim 1 wherein the treatment is carried out before irradiation.

3. The method of claim 2 wherein the compound is [Co(NH$_3$)$_4$(NO$_2$)$_2$]X where X is NO$^-_3$ or CH$_3$CO$^-_2$; [(C$_2$H$_5$)Fe]CCl$_3$CO$^-_2$·2 CCl$_3$CO$_2$H; [Co(1,10-phenanthroline)$_2$(NO$_2$)$_2$]NO$_3$H$_2$O; or [Co(diethylene triamine)(NO$_2$)$_3$.

4. A pharmaceutical composition containing a radiosensitizing amount of a Co(III) or Fe(III) coordination compound as described in claim 1.

* * * * *